US00PP27085P2

(12) United States Plant Patent
Whitcomb

(10) Patent No.: US PP27,085 P2
(45) Date of Patent: Aug. 23, 2016

(54) CRAPEMYRTLE PLANT NAMED'WHIT X'

(50) Latin Name: *Lagerstroemia indica*
Varietal Denomination: WHIT X

(71) Applicant: Carl E. Whitcomb, Stillwater, OK (US)

(72) Inventor: Carl E. Whitcomb, Stillwater, OK (US)

(73) Assignee: Lacebark, Inc., Stillwater, OK (US)

( * ) Notice: Subject to any disclaimer, the term of this patent is extended or adjusted under 35 U.S.C. 154(b) by 19 days.

(21) Appl. No.: 14/544,429

(22) Filed: Mar. 12, 2015

(51) Int. Cl.
*A01H 5/00* (2006.01)

(52) U.S. Cl.
USPC ..... Plt./252

(58) Field of Classification Search
USPC ..... Plt./252
See application file for complete search history.

*Primary Examiner* — Annette Para
(74) *Attorney, Agent, or Firm* — Jeffrey L. Streets

(57) ABSTRACT

A new and distinct variety of crapemyrtle, *Lagerstroemia indica*, particularly distinguished by having a much branched upright growth habit, a near constant show of sterile, cardinal red flowers from bright crimson flower buds during the warm growing season, with lighter red flowers during rainy periods or cooler fall conditions. Because the plant is sterile, old flowers stay showy longer and new flower buds form in the same positions as flowers that age and fall away. Inflorescences are short around the base of the plant, but are 12 to 14 inches long and 6 to 12 inches wide in the upper parts of the plant. The plant is highly resistant to both powdery mildew and *Cercospora* leaf spot under north central Oklahoma conditions.

7 Drawing Sheets

Genus, species: *Lagerstroemia indica.*
Varietal denomination: 'WHIT X'.

BACKGROUND OF THE INVENTION

1. Field of the Invention

The present invention relates to a new and distinct variety or cultivar of the ornamental shrub, *Lagerstroemia indica*, commonly known as crapemyrtle.

2. Description of the Related Art

Crapemyrtle is native to eastern China and was introduced into North America in the late 1700's. Since then this popular ornamental shrub has been grown extensive across the southern half of the continent. Over the years, seedlings of *Lagerstroemia indica* have been selected and introduced into the market with different growth habits and flower colors. In addition, hybrids between *L. indica* and *L. fauriei* have been selected to add additional features, particularly more striking bark color and resistance to powdery mildew. But, flower color of the hybrids were muted compared to seedlings of pure *L. indica.*

An assortment of methods has been utilized to develop improved varieties of crapemyrtle and several of those varieties have had U.S. Plant Patents issued. For example, U.S. Plant Pat. Nos. 4,182, 4,183, 4,184 and 4,185 disclose and claim a series of four new varieties of *Lagerstroemia indica* produced by crossing previously known varieties. Each of those varieties was characterized as having a weeping growth habit at maturity.

U.S. Plant Pat. Nos. 6,365 and 6,383 disclose varieties of crapemyrtle derived from seedling treated with a mutation-inducing chemical. It is generally known that sodium azide, colchicines and other chemicals are capable of producing plant mutations. Since only one or more of the far distant grandparents of the new variety of crapemyrtle were treated with one of these compounds, it is highly unlikely that the present invention may be a chemically induced mutation.

The new variety of crapemyrtle claimed herein, which has been given the cultivar name 'WHIT X' was selected from a block of about 12,000 seedlings planted in 2009. Parents of these 12,000 seedlings were 14, 15 or 16 generations removed from the original single seedling parent used to begin this crapemyrtle breeding program.

The specific identity of the parent of the present invention was a seedling from generation 15 with only a few seed capsules and that showed high resistance to *Cercospora* leaf spot disease which is an increasing problem where crapemyrtle are grown.

This new and distinct crapemyrtle was asexually reproduced by rooting softwood cuttings taken from the original 'WHIT X' plant near Stillwater, Okla. The asexually reproduced plants show all of the unique features that characterize this crapemyrtle including high disease resistance, thereby indicating that the unique features of this plant are stable through successive generations of asexual reproduction. Softwood cuttings taken from our new variety of crapemyrtle were successfully rooted under intermittent mist. Subsequent cuttings from plants produced from previous cuttings from the 'WHIT X' original parent have also been rooted. Growth, flowering, flower and foliage color and capacity to rebloom on old inflorescences with no seed production and high degree of resistance to both powdery mildew and *Cercospora* leaf spot remain consistent with the parent.

SUMMARY OF THE INVENTION

The plant of the present invention is a new and distinct variety of crapemyrtle, *Lagerstroemia indica* which has been given the cultivar name 'WHIT X' and is characterized by a much branched growth habit with moderate vigor that may reach a height of 8 to 10 feet if left unpruned. The original 'WHIT X', now 6 years old, was killed to the ground in 2011, when temperatures dropped to an unprecedented −19 F, but regrowth was vigorous and is now about 5 feet tall by 28 inches wide. Cuttings taken from the parent following the complete top kill, rooted and grew the same as plants propagated from before the severe cold, confirming that no genetic change occurred.

Leaves of the plant emerge dark red-purple and remain dark purple-green. Mature leaves are typical in size and shape as the species. Twigs of current season growth emerge dark red-purple and remain of similar color until growth slows near the end of the growing season when they become light tan.

Inflorescences are between about 12 to 14 inches long and between 6 to 12 inches wide in the upper part of the plant. Flower buds are crimson. Individual flowers are cardinal red in full sun and during temperatures above about 85 degrees F. However, flowers that open during cloudy days emerge lighter red, but with return of full sun and warm temperatures, flowers will change to cardinal red. In late summer and temperatures below about 80 degrees F. flowers open and remain light red. Flowers remain showy for 14 to 20 days in Oklahoma, do not blacken along the margins and drop cleanly. Flower petals typically fold over so that few stamens are visible, however, the few that are exposed are bright yellow.

Flowers are sterile.

Each inflorescence typically produces a full flower show, then as the flowers age and fall, new flower buds quickly form in the locations of the previous flowers. In addition, production of new stems during the growing season and terminating in panicles of blooms also adds to and prolongs the flower show. Unless checked by severe drought or other environmental or cultural problem, flowering typically begins in late June in North Central Oklahoma and flowering continues until frost.

DETAILED BOTANICAL DESCRIPTION

The following botanical description is of the new and distinct cultivar of crapemyrtle, *Lagerstroemia indica*, which has been given the cultivar name 'WHIT X'. Specific color designations set forth by number designations are in accordance with The Royal Horticultural Society Colour Chart (1966). General color recitations are consistent with ordinary American color terminology.

The crapemyrtle cultivar 'WHIT X' has not been observed under all possible environmental conditions. It is to be understood that the phenotype may vary significantly with variations in environment such as soils, temperature, light intensity and length of day without differences in the genotype of the plant. The following botanical characteristics and observations are taken from plants when grown under normal outdoor conditions in north central Oklahoma. Unless otherwise noted, the following description is of plants propagated from the original parent plant and are four years old, growing in a field near Stillwater, Okla., but is also consistent with plants ranging from a few months to 18 months growing in containers in north central Oklahoma.

The plant:

*Type*.—Deciduous, upright, woody shrub with multiple stems and dense branching.

*Classification*.—Crapemyrtle, *Lagerstroemia indica*.

Figure 1:
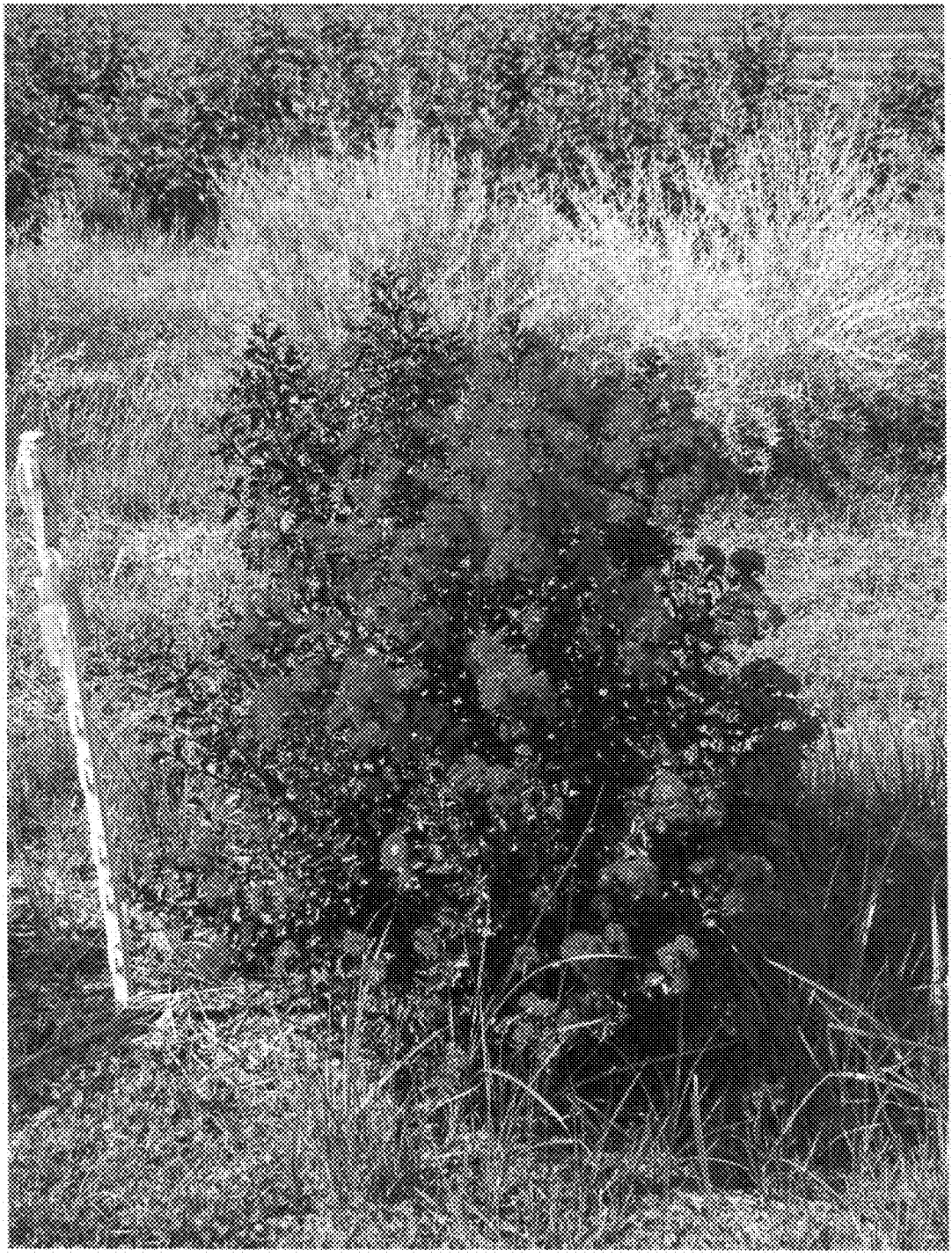
FIG. 1 is a full color photographic view of the new crapemyrtle plant 'WHIT X', showing its growth and flowering habit near Stillwater, Okla.
Figure 4:
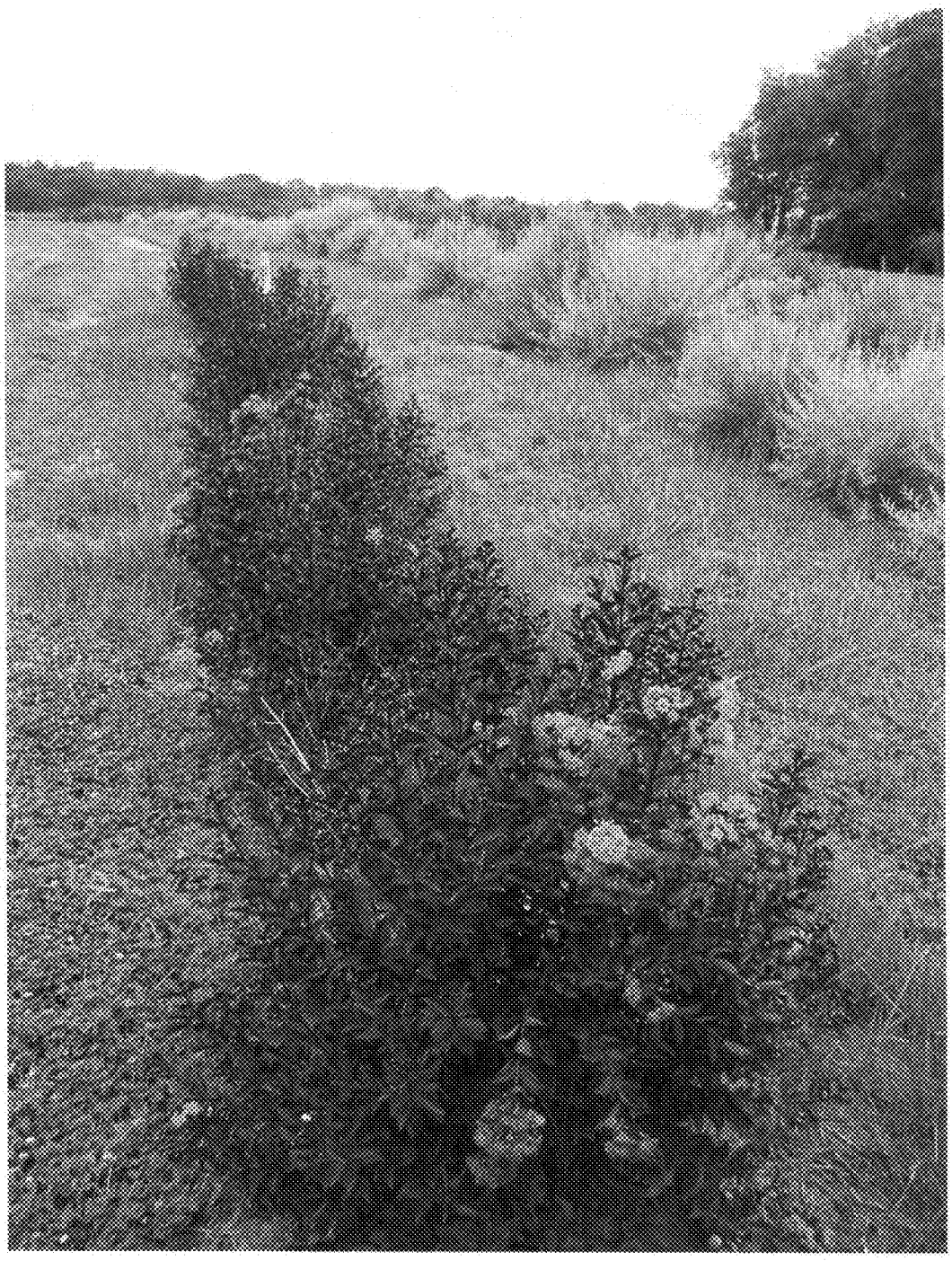
FIG. 4 is a full color photographic view of a row of 'WHIT X' plants showing red-purple new growth and flowers partially dark red and partially light red, following cloudy days and rain.

*Growth habit*.—The plant is a moderate grower with prolific branching. Vegetative growth is moderate in spring and continues into late summer. Flowering begins in late June in north central Oklahoma. Unlike other crapemyrtle varieties from this breeding program, such as crapemyrtle described in U.S. Plant Pat. Nos. 10,296 and 11,342 which produce little new growth once flowering begins, 'WHIT X' of the present invention typically produces some new vegetative growth adjacent to full flowering inflorescences as shown in FIG.1 and FIG. 4.

*Origin*.—An open pollinated cross in a crapemyrtle selection/breeding program near Stillwater, Okla.

*Propagation*.—The plant is easy to propagate from softwood cutting under mist, with the distinguishing characteristics of the asexually propagated offspring remaining identical to the parent.

*Size and shape*.—The original parent was killed to the ground in February 2011 due to unprecedented cold of —19 F. Plants propagated from new growth from the original parent average about 4 feet tall with a spread of 28 to 36 inches creating a broad, upright shrub at age four years in the field as shown in FIG. 1. Based on growth rate of the four year old plants in the field, it is estimated that 'WHIT X' may reach a height of 8 to 10 feet and spread of 5 to 7 feet.

*Hardiness*.—The new variety of crapemyrtle has withstood temperature of about 0 degrees F. in the field with no injury.

*Pests and disease*.—The foliage has been very resistant to powdery mildew and *Cercospora* leaf spot.

Figure 7:
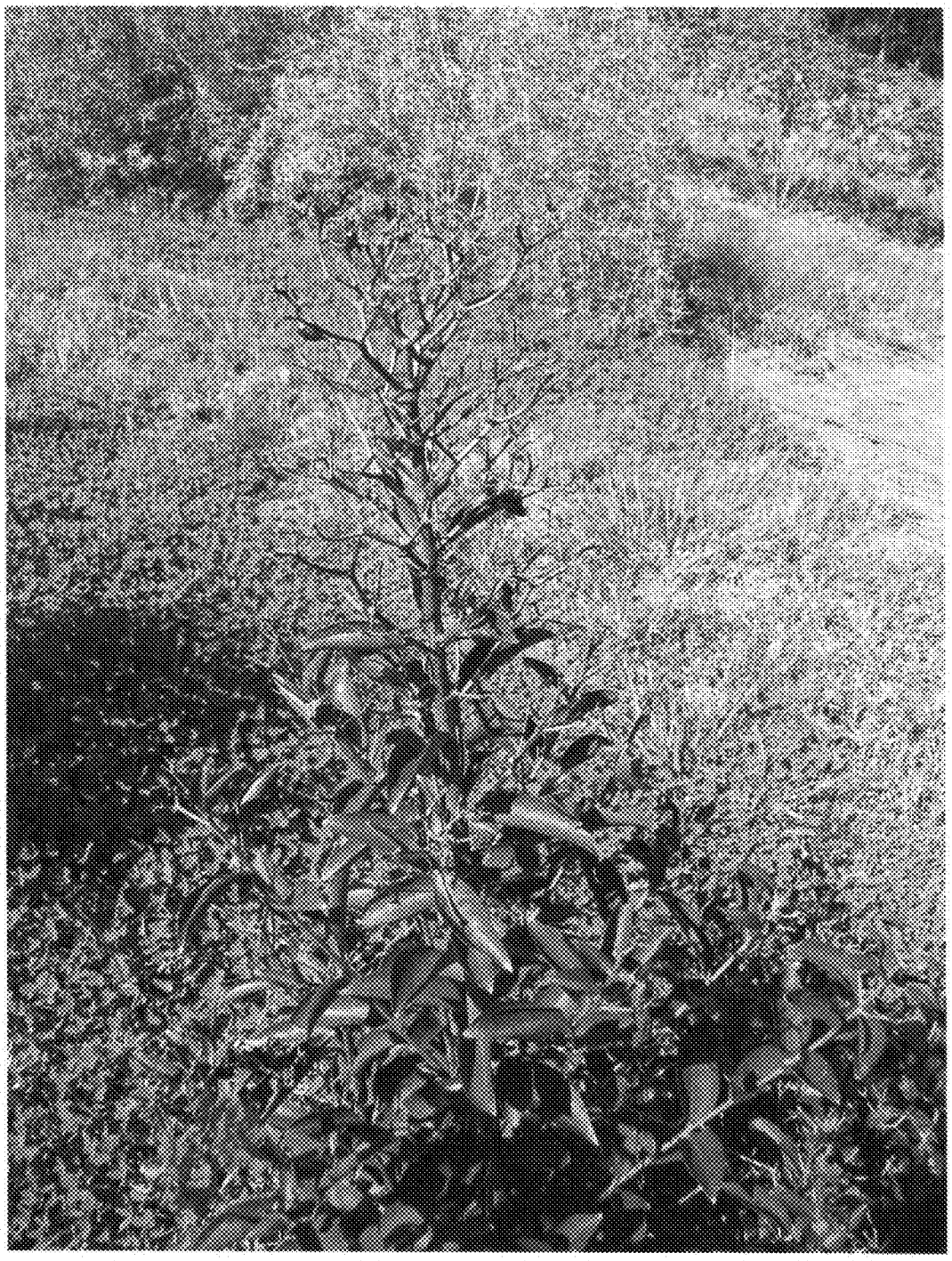
FIG. 7 is a full color photographic view of an inflorescence and mature foliage near the end of the growing season.

The flowers:

*Blooming period*.—Blooming begins in late June and continues into October in north central Oklahoma. This flowering period is longer than most seedlings and cultivars of crapemyrtle known to me. Flowering continues during periods of intense and prolonged heat as long as moisture is available. Because the plant is sterile, flowers remain showy longer and after flowers age and fall from positions in the inflorescence, new flower buds are produced in the same location. Typically five or more sets of flowers are produced on each inflorescence or until late season cool weather stops the flower bud cycling as shown in FIG. 7. This unusual flower production sequence makes the flower show near continuous and removes peaks of flower show then seed production, as occurs with conventional crapemyrtle. Individual flowers typically remain attractive for 14 to 20 days unless moisture is severely limiting.

Figure 3:
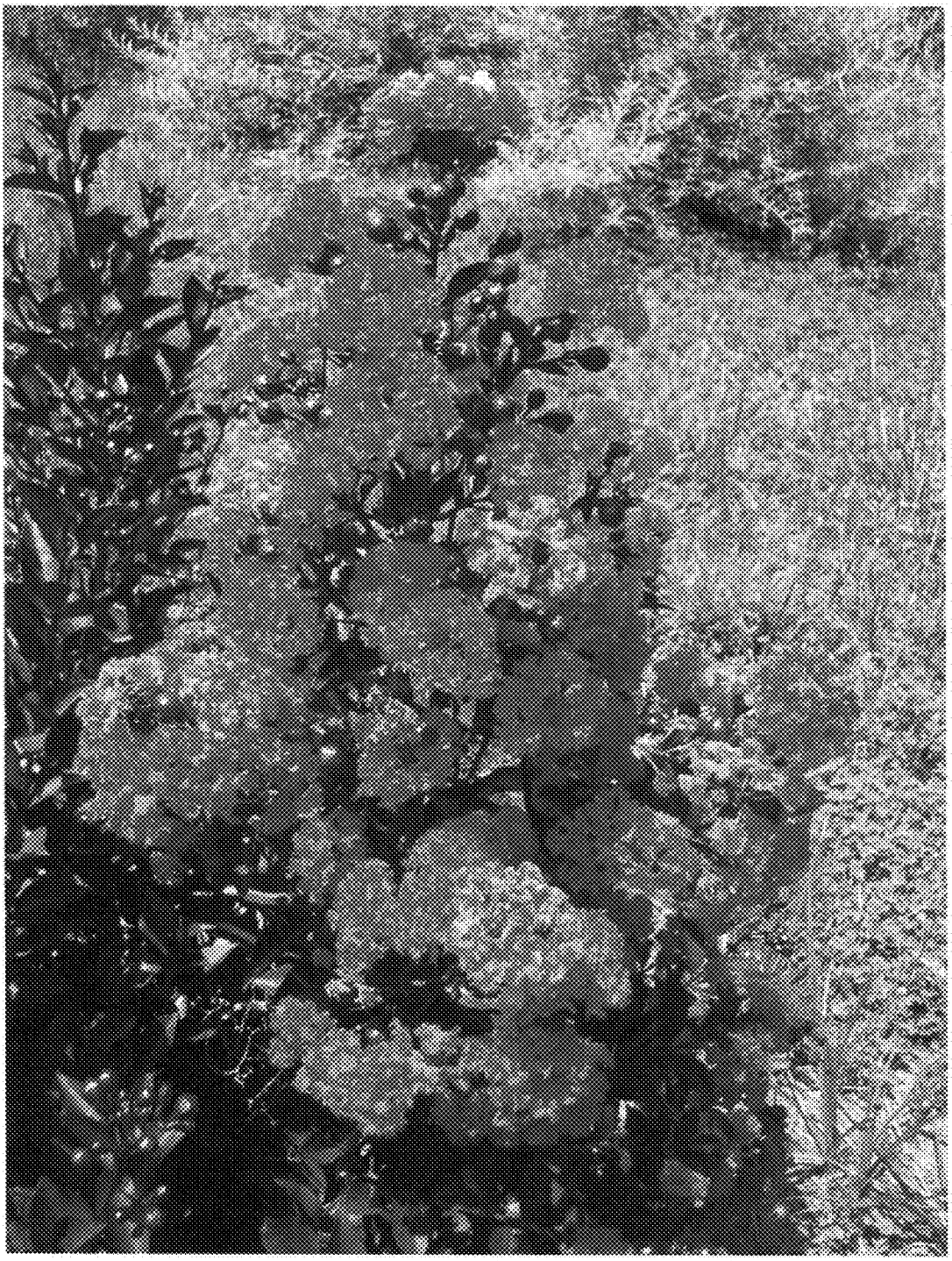
FIG. 3 is a full color photographic view of an inflorescence with most flowers open.

*Petals*.—Blades of individual newly opened petals (expanded apical portion) are cardinal red (53 A) when open with full sun and temperatures above 85 degrees F. during the day. With moderately cooler temperatures, for example 75 to 80 degrees and some cloud cover, flowers are typically lighter (53 B or C), however, when full sun and warmer conditions return, flowers will darken (53 A). With the arrival of early fall and temperatures in the range of 60 to 70 degrees F. during the day and cooler at night, flowers typically open light red (53 B, C or D) with only modest darkening with the return of warmer days and full sun (For example, flowers may open 53 C and then darken to 53 B or later in the season from 53 D to 53 C or B.) Overall the flower petal shape is more or less orbicular with an uneven and irregular undulating surface and about ½ to 1 inch across. The petal claw (the narrow stalk-like basal portion of the petal) is also cardinal red during the summer (53 B or C) and about ¼ inch long. The flower petals, typically 6, but occasionally 5 or 7, open only partially on most flowers creating a dense cluster of petals as shown in FIG. 3 and obscure the stamens. Stamens range from 10 to 30 upon careful inspection but are only rarely exposed by the petals. When anthers are present they are about 1/16 inch long, yellow, approx 15 A. Filaments are approx. ⅛ inch long. Most flowers have no anthers, only an entangled mass of filaments. As flowers age, the entire perianth of petals and sepals typically fall cleanly as a unit from the inflorescence and without discoloring or becoming unattractive.

*Inflorescences*.—The inflorescences are panicles from about 4 inches long and 3 inches wide near the base of a plant to 12 to 14 inches long and from 6 to 12 inches wide in the upper portion and contain from 15 to 250 buds or flowers. The stocks of inflorescences (peduncle) exposed to full sun are purplish (187 A or B) mid-summer with max light intensity or lighter (187 B, C or D) later in the season when nights begin to cool. However, after being partially or mostly shaded by flowers for 14 to 20 days, stocks are lighter in color (187 C or D to 186 A or B). Because of the complex and irregular branching of the inflorescence in FIGS. 2 and 3, precise assignments of colors to structural parts is difficult.

*Stamens*.—An occasional flower has distinct yellow stamens (15 A), but more common are a complex of twisted and deformed stamens mostly retained in the flower bud.

*Sepals*.—There are typically six sepals per bloom, each having the shape of one-sixth of a sphere and each about 5/16 to 7/16 long.

Figure 2:
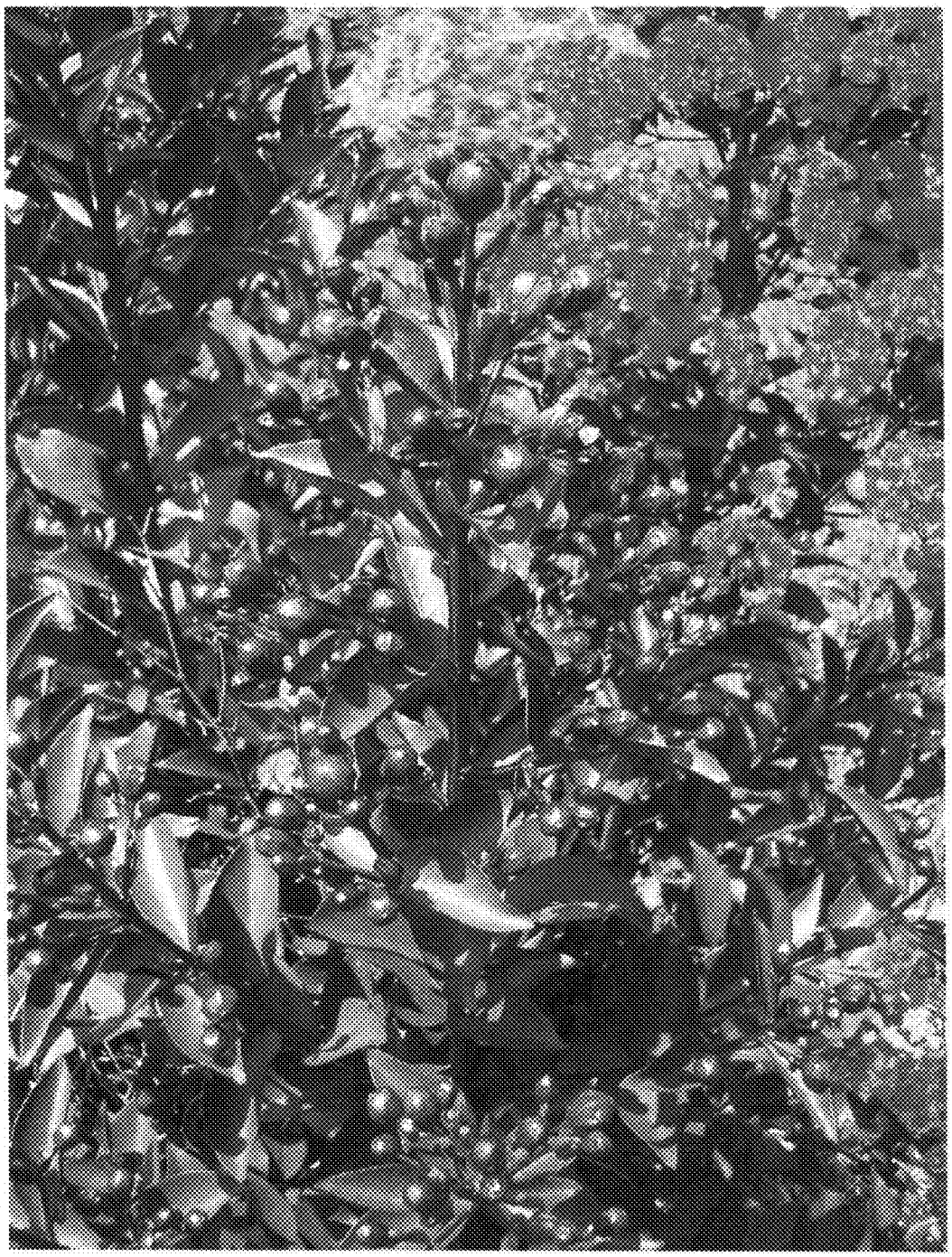
FIG. 2 is a full color photographic view of an inflorescence with crimson flower buds ready to open in the center and another in full flower to the upper right.

*Buds*.—Unopened flower buds are round with six distinct lines of dehiscence where they split to allow flower petals to expand. Bud size increases with age to typically between 3/16 to 5/16 inch diameter. The unopened flower buds are typically dark crimson (187 A in direct sun to slightly lighter (187 B or C where buds are partially shaded as shown in FIGS. 2 and 3.

*Seeds*.—The plant it sterile.

Figure 5:
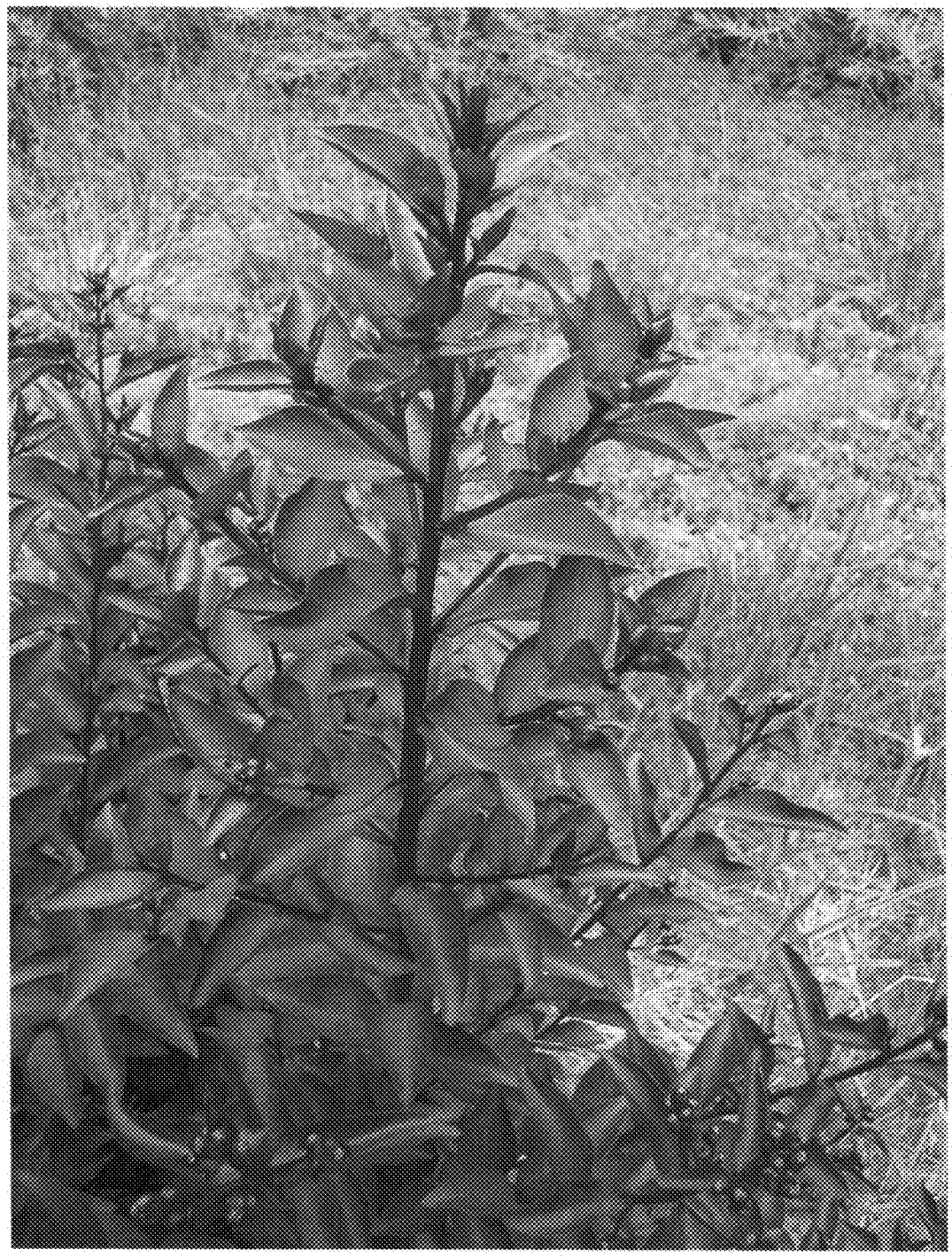
FIG. 5 is a full color photographic view of red-purple new foliage and stems.
Figure 6:
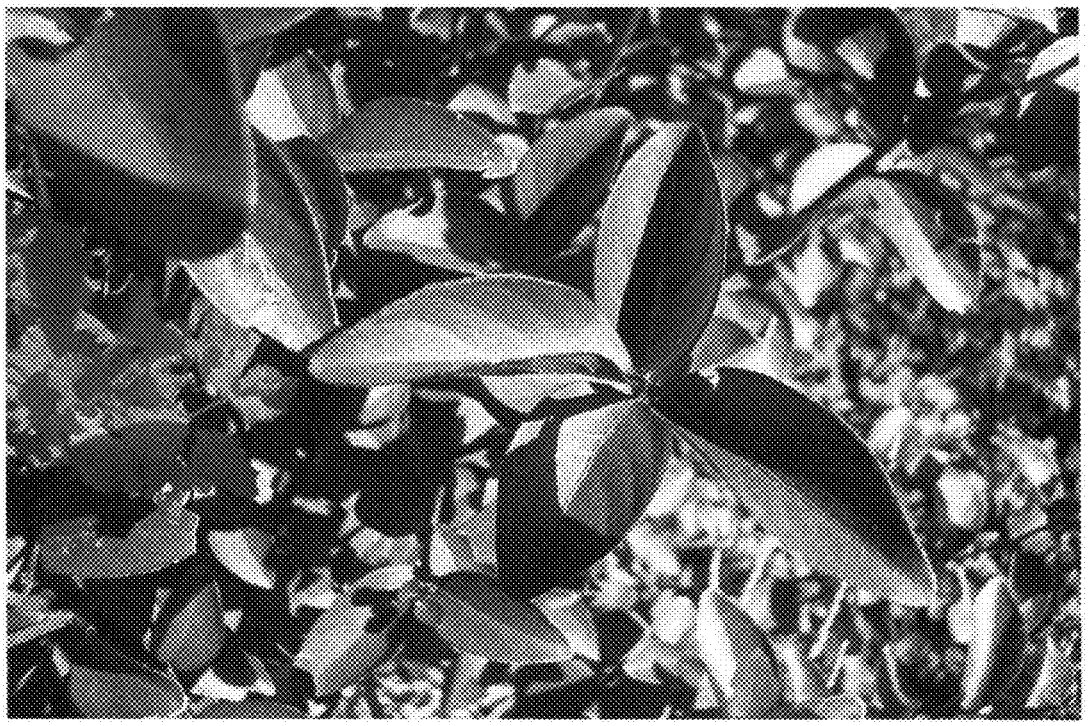
FIG. 6 is a full color photographic view of mature leaves.

The foliage:

*Leaf shape*.—The leaf shapes range from ovate and acute at the tip to broadly lanceolate as shown in FIGS. 5 and 6 with a smooth margin. The leaf petiole is typically absent or very short and not distinct.

*Leaf color*.—The upper and lower surfaces, including midribs below of new leaves emerge glossy dark reddish-purple, grayed-purple group (187 A or B) and remain so for several weeks as shown in FIGS. 1, 4 and 5, slowly transitioning to 187 B, with slight increasing of green. Mature leaves have a dull purple cast with slight increase in green when heavily shaded (no color match among R.H.S. Colour Chart), FIG. 6 and finally, fully shaded old leaves become dull, dark mostly green with a touch of purple (147 A) but this is a poor match. The plant is typically still in full flowering mode with the arrival of first frost, such that there is no fall color.

*Leaf texture*.—Mature leaves are smooth on both upper and lower surfaces, becoming more thick and leathery with age.

*Leaf size*.—Leaf size increases with age, reach a typical length of about 1½ to 2½ inches long and between about ¾ to 1¼ inches wide, with the widest point near the center.

The branches and bark:

*Branch color*.—The current seasons new growth exposed to direct light is red-purple (187 A, B or C), FIGS. 1, 4 and 5, transitioning to a lighter color with age and maturity (187 C or D), then becoming tan with a bit of purple tint, greyed-orange group (177 C or D) then gradually a more tan (166 B or C) and finally, dormant stems are darker tan (165 A), FIG. 7.

*Branch length*.—Branch length is dependent on growing conditions of the plant, and typically range from between 3 to 4 inches at tips of lower branches, to 12 to 18 inches for upright branches as shown in FIGS. 4 and 5.

*Branch diameter*.—Diameter of a current season's growth ranges from between about ¼ to 7/16 inch.

*Bark*.—The bark of mature stems and branches is a dark tan (165 A) as shown in FIG. 7. Unlike a typical crapemyrtle, the base of the oldest stems has yet to begin to exfoliate.

I claim:

1. A new and distinct variety of crapemyrtle plant, substantially as illustrated and described.

* * * * *